United States Patent [19]
Taylor

[11] Patent Number: 5,663,565
[45] Date of Patent: Sep. 2, 1997

[54] SYSTEM AND METHOD FOR THE ON-LINE MEASUREMENT OF KEY GLUE-LINE CHARACTERISTICS ON CORRUGATED BOARD

[75] Inventor: Bruce F. Taylor, Worthington, Ohio

[73] Assignee: Qualitek Limited, Worthington, Ohio

[21] Appl. No.: 447,701

[22] Filed: May 23, 1995

[51] Int. Cl.$^6$ ............................................. G01N 21/35
[52] U.S. Cl. ........................ 250/339.11; 250/339.12; 250/359.1; 156/64
[58] Field of Search .................... 250/339.11, 339.12, 250/339.04, 341.8, 359.1; 156/64, 208

[56] References Cited

U.S. PATENT DOCUMENTS

| | | | |
|---|---|---|---|
| 3,150,264 | 9/1964 | Ehlert | 250/339.11 |
| 4,497,027 | 1/1985 | McGuire et al. | 364/471 |
| 4,806,183 | 2/1989 | Williams | 156/64 |
| 4,840,706 | 6/1989 | Campbell | 250/339.11 |
| 5,049,216 | 9/1991 | Shead et al. | 156/64 |

*Primary Examiner*—Carolyn E. Fields
*Attorney, Agent, or Firm*—Hale and Dorr

[57] ABSTRACT

The system and method of the present invention determines glue-line characteristics, such as temperature, of corrugated board. Components of an on-line glue sensor's output signal that are oscillating at the fluting frequency are isolated. The components of the sensor output signal that are sensitive to glue, which is only present on the tips of the flutes, oscillate at the fluting frequency. Those variations in the sensor output signal that are not oscillating at the fluting frequency are canceled out, while those that are oscillating at the fluting frequency are isolated and amplified, facilitating an accurate estimate of their amplitude. The output signal of an infrared absorption sensor will provide an improved on-line starch measurement for corrugators. The incremental amount of infrared radiation that is absorbed by starch and/or water in the glue-lines is isolated from the predominant, more random background absorption due to cellulose and water in the paper substrate. The amplitude of the extracted signal component, which reflects only the starch and/or water in the glue, is then converted using empirically derived calibration constants into a final starch mass value.

26 Claims, 13 Drawing Sheets

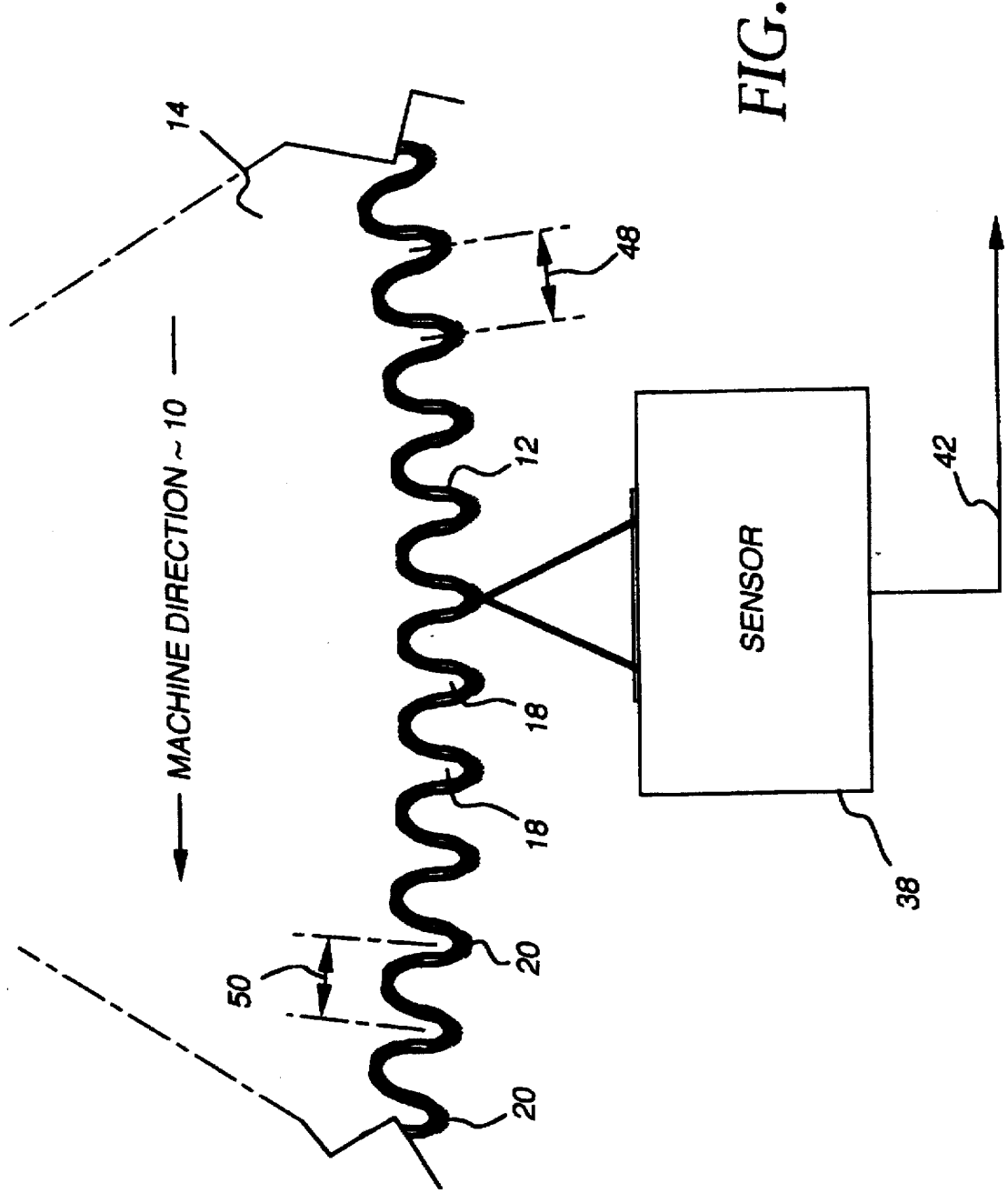

Integrated Values (using 1st and 2nd reference signals)

RSS Values and Filtered Final Values

MACHINE DIRECTION ~ 10

SYSTEM AND METHOD FOR THE ON-LINE MEASUREMENT OF KEY GLUE-LINE CHARACTERISTICS ON CORRUGATED BOARD

BACKGROUND OF THE INVENTION

This invention relates to a system and method for measuring characteristics of corrugated board and, more particularly, a system and method for measuring glue-line characteristics on such corrugated board.

Corrugated board is formed by bonding, with a starch-based, aqueous glue, one or more layers of paper, called liner, to the outside of one or more fluted paper layers, called medium. The medium is first passed between two fluted, heated rolls (corrugating rolls) which deform it into the desired fluted shape. Glue, consisting primarily of starch and water, is then applied to the top of the medium's flutes, after which it is bonded to the top liner to form the singleface web. Glue is then applied to the bottom of the singleface web's flutes before it is finally bonded to the bottom liner to form the finished board. To achieve acceptable bond strength, and to minimize glue consumption, a uniform application of glue is preferred with respect to both time and cross-machine position (across the machine's width). To ensure acceptable bonding the temperature of the glue during and after its application to the flute tips should also fall within a preferred range.

Improving the uniformity of glue application, with respect to both time and cross-machine position allows the glue consumption rate to be reduced. Reducing glue consumption provides numerous benefits. A typical corrugating machine, producing about 3,100 tons of board per month, will consume about 125,000 lbs of glue per month, which represents a significant raw material expense. The applied glue is also about 80% water, about three quarters of which must be dried out of the board by steam-filled hot-plates after the board is formed. The energy used to generate this steam also represents a significant expense. In addition, board warp (which generates sub-standard board that must be scrapped) is caused by moisture gradients within the board, which are aggravated by excessive glue application.

By measuring the starch mass and/or its temperature following application, with respect to both time and cross-machine position, irregularities can be detected and corrected, providing more uniform glue application to increase board strength and reduce glue purchases, energy use, and board scrap.

To date, no on-line glue measurement techniques have been successfully commercialized. A recognized, potential technique would use the principle of infrared absorption to indirectly measure the starch mass after its application. The basic principles of this sensor technology are described in numerous documents, including U.S. Pat. No. 5,049,216. However, the primary infrared absorption band for starch overlaps that of cellulose, and the ratio of starch mass to the background paper mass is so small (about 2.5 lbs of starch per 125 lbs of board) that the glue component cannot be identified with adequate precision using conventional techniques (even a significant 5% variation in starch mass would typically represent a total fluctuation of only about 0.1% of a corrugated board's total mass).

To measure the glue's temperature close to the point of bonding, the temperature of the glue must be measured shortly after it has been applied to the medium. However, the difference between the temperature of the glue and that of the paper behind it cannot be detected with conventional non-contact temperature sensors such as infrared pyrometers, which are based on the principle of passive infrared emission (in a conventional application of an infrared pyrometer the sensor would measure the average temperature of the glue-covered surface).

The glue's starch is deposited only on the flute tips of the medium, forming glue-lines which span the width of the machine. To amplify a glue measurement signal (whether it is representative of the starch mass or glue temperature), and isolate it from a board background measurement signal, the measurement must be localized on the glue-lines. However, conventional sensor technologies are incapable of localizing the measurement along the glue-lines, which are typically only about 0.04 inches long in the machine-direction, and which will pass a given point on the machine at the rate of about 1,000 glue-lines per second, for a machine speed of 1,000 feet/minute.

It is therefore a principle object of the present invention to provide a system and method for measuring glue-line characteristics on corrugated board.

It is a further object of the present invention to measure glue-line characteristics on corrugated board during the manufacture of such corrugated board.

Still another object of the present invention is to provide a system and method for the on-line measurement of the uniformity of glue application during the manufacture of corrugated board.

SUMMARY OF THE INVENTION

Accordingly the system and method of the present invention use common sensor technologies such as infrared absorption and/or passive infrared emission to successfully measure the mass distribution and/or temperature, respectively, of a starch-based glue that has been applied to the fluted medium of a corrugated board. This is achieved by a signal processing method that may be referred to as phase-locking, which exploits the fact that the glue-line measurement signal oscillates at a known fluting frequency (which is a function of the flute pitch and the machine speed) to isolate the glue-line measurement signal (whether it is representative of the mass or temperature of the glue) from the background measurement signal of the paper substrate.

The system and method of the present invention process a suitable output signal from a sensor to determine the amplitude of repetitive, high-frequency (typically 500 to 1,000 Hz), glue-based variations, which, being due to the glue-lines, oscillate at the fluting frequency. The fluting frequency is equal to the monitored machine speed divided by the known, constant flute pitch. Isolating the glue-based variations is accomplished by narrow band-pass filtering, using a suitable implementation of a signal processing technique referred to as phase-locking. This method isolates that component of the sensor output signal that is oscillating at the known fluting frequency, by filtering-out less repetitive, and/or lower frequency, variations that are a function of the characteristics of the paper-based substrate.

The measurement signal is typically generated by either an infrared absorption sensor, which is used to measure the mass of moisture and/or starch in the glue-line, or an infrared pyrometer, which is used to measure the temperature of the glue-line. The chosen sensor is installed so as to measure the exposed glue-line prior to bonding of the medium with the liner.

The sensor is preferably mounted to a traversing mechanism that carries it back and forth across the width of the corrugating machine. Measurement can thus be made of the characteristics of a glue-line at a plurality of points across the machine width so as to develop a cross-machine profile of the chosen glue-line characteristic. The average of all measurements taken across the machine width may also be derived for each traverse, then the results of sequential traverses analyzed to determine the machine-direction, or time-dependent variation of the chosen glue-line characteristic. The machine-direction glue mass measurement may also be compared to the monitored total glue consumption rate (which is provided by a mass flow measurement device located in the supply line of the glue applicator) to facilitate automated, periodic, on-line calibration of the traversing glue mass measurement.

These and other features and objects of the present invention will be more fully understood from the following detailed description which should be read in light of the accompanying drawings in which corresponding reference numerals refer to corresponding parts through the several views.

BRIEF DESCRIPTION OF THE DRAWINGS

FIG. 3a is a side elevational schematic view of an angular segment of a corrugating roll, showing the relative placement of a measurement sensor utilized in the system and method of the present invention.

DETAILED DESCRIPTION OF THE DRAWINGS

Figure 1:
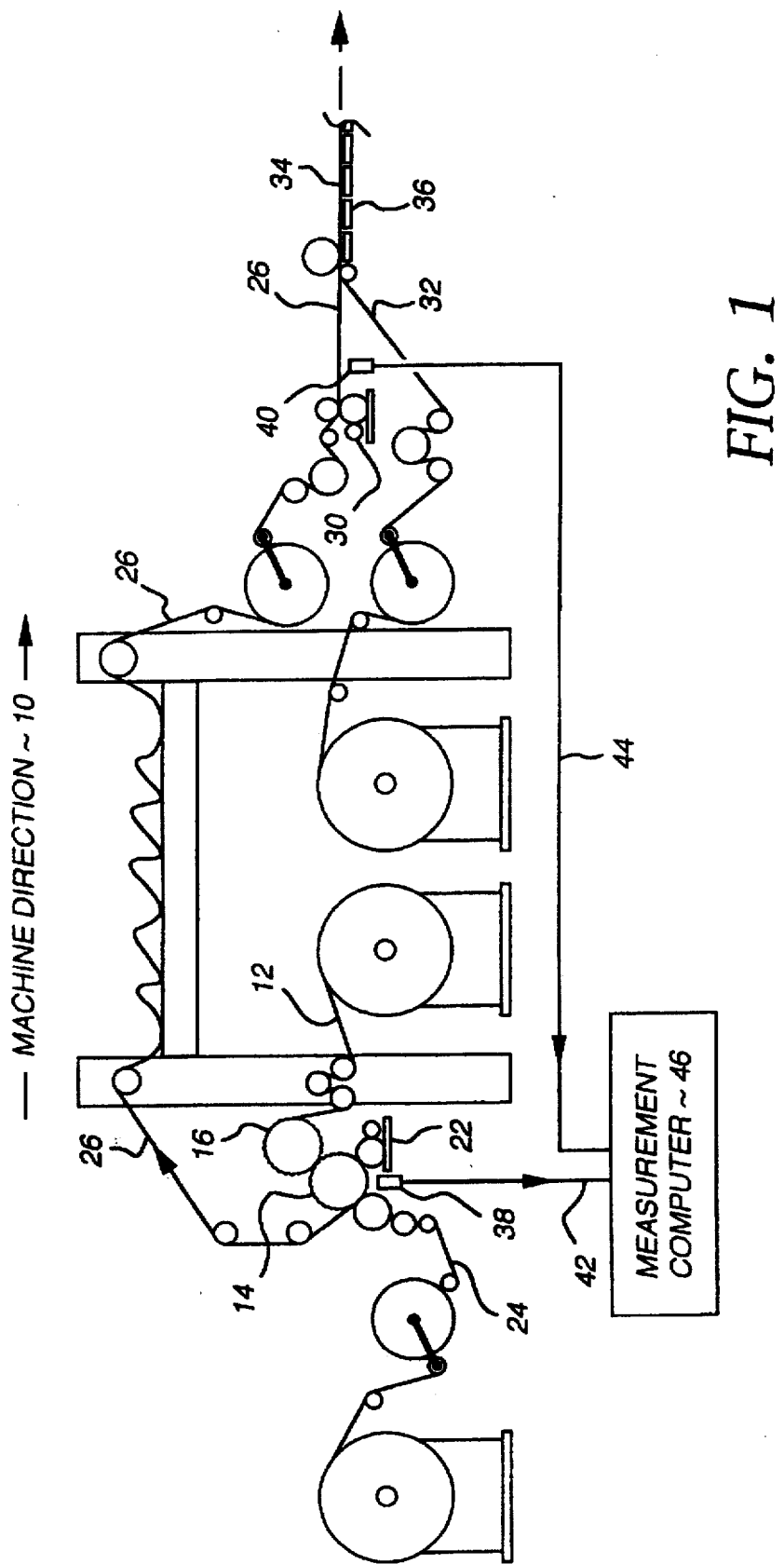
FIG. 1 is a side elevational schematic view of a corrugating machine, showing preferred placements of the sensors utilized by the system and method of the present invention as well as the location of relevant corrugating machine components.
Figure 2A:
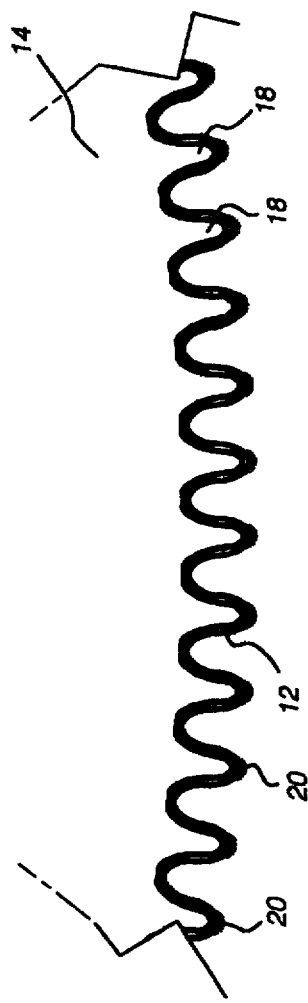
FIG. 2a is a side elevational view of an angular segment of a corrugating roll, showing the fluted medium lying flush with the surface of the fluted corrugating roll.
Figure 2B:
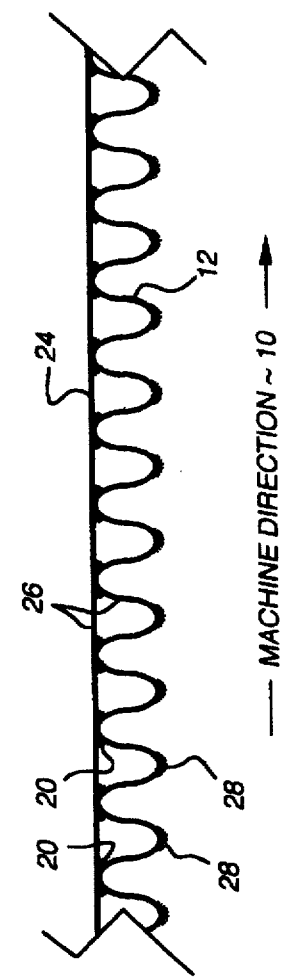
FIG. 2b is a side elevational view of a machine-direction segment of a singleface web, showing the singleface liner bonded to the fluted medium.
Figure 2C:
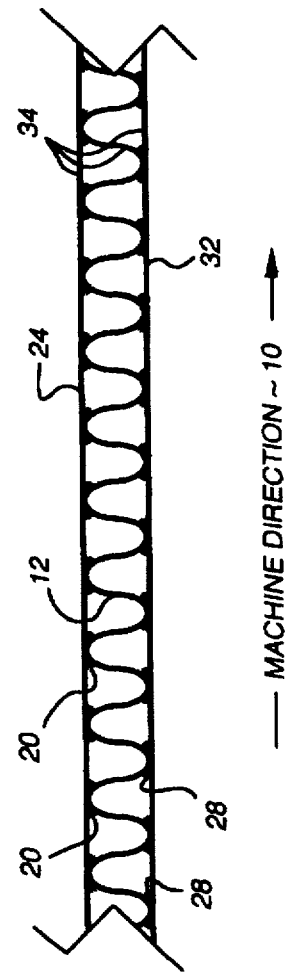
FIG. 2c is a side elevational view of a machine-direction segment of combined board, showing the external singleface and doubleface liners bonded to the internal fluted medium.

Referring now to FIGS. 1, 2a, 2b and 2c corrugated board is manufactured by bonding outer layers of paper (the liners) to an inner layer of fluted paper (the medium). As it travels in the machine-direction 10, the medium 12 is first passed between two toothed, heated, fluting rolls 14, 16, whose teeth 18 deform the medium 12 into the desired fluted shape. Glue-lines 20 consisting primarily of starch and water, are then applied to the top of the medium's flutes by the first glue applicator 22 (also referred to as the singleface glue applicator), after which the medium 12 is bonded to the top liner 24 (also referred to as the singleface liner) to form a composite web 26 (also referred to as the singleface web). Glue-lines 28 are then applied at the second glue applicator 30 (also referred to as the glue station) to the bottom surface of the fluted medium 12, before the singleface web 26 is finally bonded to the bottom liner 32 (also referred to as the doubleface liner) to form the corrugated board 34. After the liners 24, 32 and the medium 12 are joined, the board 34 is dried at elevated temperature in the hot-plate section 36 to set the starch-based glue.

Figure 3B:
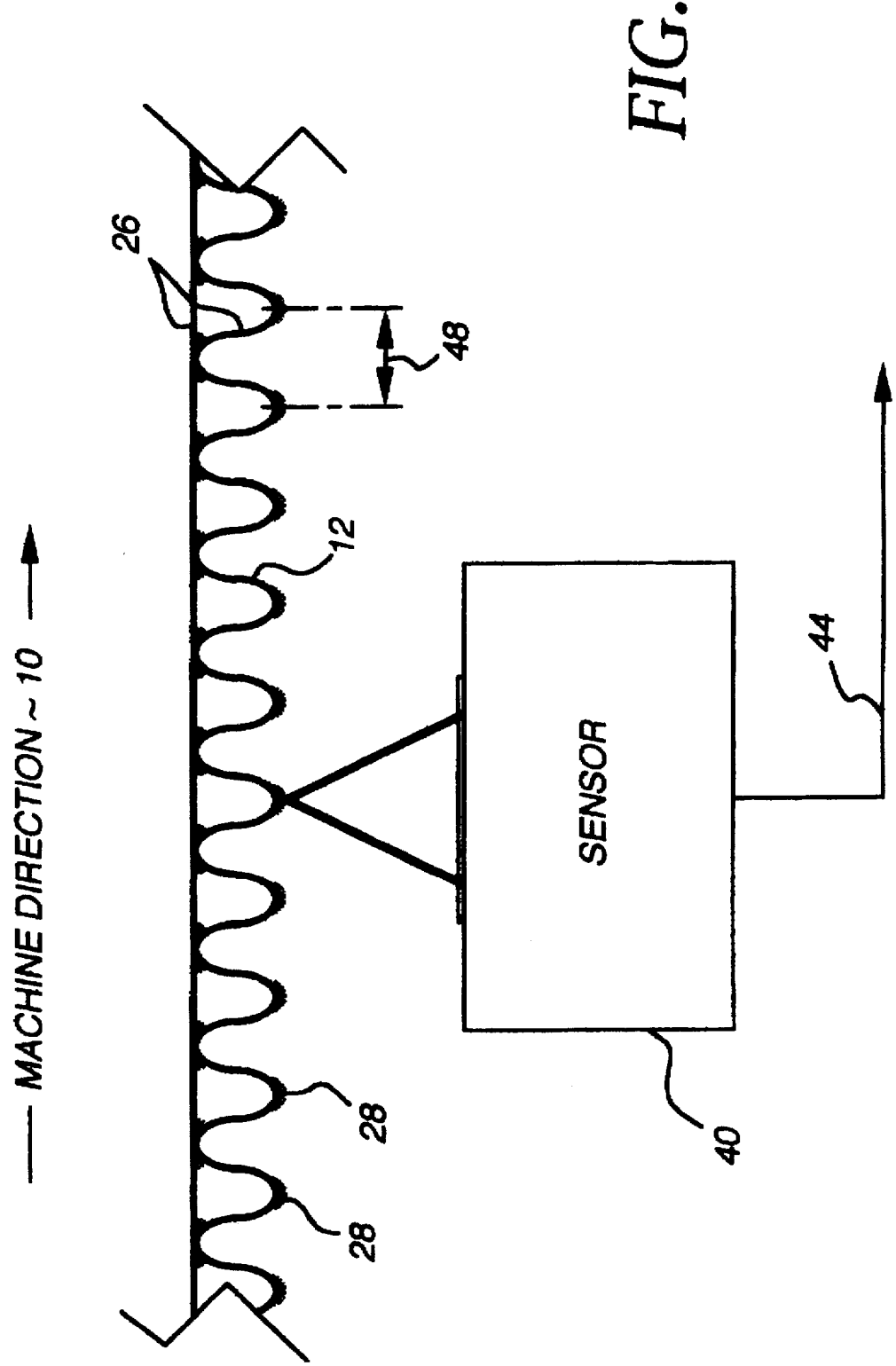
FIG. 3b is a side elevational schematic view of a machine-direction segment of a singleface web, showing the relative placement of a measurement sensor utilized in the system and method of the present invention.

Referring now to FIGS. 1 and 3a, the system and method of the present invention employ one or more sensors 38 located below and adjacent to the fluting roll 14, to measure the glue-lines 20 which are located on the exposed, fluted surface of the medium 12. The sensor(s) 38 would thus measure the characteristics of the glue-lines 20 which are used to bond the singleface liner 24 to the medium 12. Referring now to FIGS. 1 and 3b, the system and method of the present invention may also employ one or more sensors 40 located below and adjacent to the underside of the singleface web 26, and downstream of the glue station 30, but upstream of the hot-plate section 36, so as to measure the glue-lines 28 which are located on the exposed bottom surface of the fluted medium 12. The sensor(s) 40 would thus measure the characteristics of the glue-lines 28 which are used to bond the singleface web 26 to the doubleface liner 32.

Referring now to FIGS. 1, 3a, and 3b, the output signals 42, 44 from each of the sensors 38, 40 are independently processed by a measurement computer 46 which uses a software-based narrow band-pass filtering procedure to isolate that component of each sensors output signal 42, 44 that is oscillating at the fluting frequency. The fluting frequency is a simple function of the machine speed and the glue-line interval 48 (which is equal to the pitch 50 of the teeth 18 on the fluting rolls 14, 16). For example, if the glue-line interval 48 is 0.2 inches, and the machine speed is 1,000 feet/minute, then the glue-lines 20, 28 will pass by the sensors 38, 40 at the rate of 1,000 glue-lines/second (i.e. 1,000×12/(60×0.20) =1,000 Hz). The repeatable fluctuations in the sensor output signals 42, 44 caused by the passage of glue-lines 20, 28 are superimposed upon typically larger, more random signal variations which, in the case of starch measurement, may be caused by variations in the basis weight and moisture of the singleface liner 24, medium 12, and doubleface liner 32. Differentiating glue-line signal components from background signal components is accomplished by a suitable narrow band-pass filtering procedure, which reliably isolates those components of the sensor output signals 42, 44 that are fluctuating at the fluting frequency. Variations of a common signal processing technique referred to as phase-locking are preferred for this purpose.

Referring now to FIG. 4 and FIGS. 5a through 5k, the following description of a particular implementation of the preferred phase-locking procedure should be understood to be one possible procedure and modifications to this signal processing procedure could be made without altering the end result or the objects of the present invention. The preferred phase-locking procedure may be demonstrated by the treatment of a representative sensor output signal "g(t)" 42 (FIGS. 4 and 5a) as described by mathematical and graphical representations of each step in the analytic process. The sensor output signal "g(t)" 42 used in the following example consists of three sinusoidal components, a low-frequency component "$g_1(t)$" 52 (FIG. 5b) which reflects long-term variations in the paper's moisture, weight, or temperature, a medium-frequency component 54 "$g_2(t)$" (FIG. 5c) which reflects short-term variations in the paper's moisture, weight, or temperature, and a high-frequency component "$g_3(t)$" 56 (FIG. 5d) which is representative of the measured glue-line characteristic (i.e. starch content or differential temperature, which is the difference between the glue-line's temperature and that of the paper substrate) whose amplitude "$A_3$" 58 (FIG. 5d) is to be determined. The sensor output signal 42 of this example may therefore be represented by the following relationship;

$$g(t)=\Sigma g_n(t)=\Sigma(A_n/2)\times\cos(\omega_n\times t)\times D_n,$$

for n=1 to N (where N=3 for this example)

Where; $A_n$=Amplitude of component "n" (defined as the peak-to-valley value)

$\omega_n$=Frequency of component "n" (cycles per seconds)

$D_n$=DC offset of component "n"

Therefore;

$$g(t)=g_1(t)+g_2(t)+g_3(t),$$

where;

$$g_1(t)=(A_1/2)\times\cos(\omega_1\times t)+D_1$$

$$g_2(t)=(A_2/2)\times\cos(\omega_2\times t)+D_2$$

$$g_3(t)=(A_3/2)\times 33\cos(\omega_3\times t)+D_3$$

To simplify the following description, the high-frequency component 56, its frequency "$\omega_3$" and its amplitude 58, shall henceforth be referred to as the glue-line component 56, the fluting frequency, and the glue-line amplitude 58, respectively.

The y-axis scale (i.e. the ordinate) of the graphs in this example are given as "% of scale", as in practice the appropriate absolute scaling of the sensor output signal 42 would depend on the specific sensor type and the glue-line characteristic it is measuring (i.e. starch content or differential temperature). In this example the glue-line amplitude "$A_3$" 58 is set to 3% of full scale, while the amplitude "$A_1$" 60 of the low-frequency component 52, and the amplitude "$A_2$" 62 of the medium-frequency component 54, are set to 25% and 8% of full scale, respectively. In addition, the DC offset "$D_3$" 64 of the glue-line component 56 is, by definition, set to half the glue-line amplitude "$A_3$" 58 (or 1.5% of full scale), while the DC offset "$D_1$" 66 of the low-frequency component 52, and the DC offset "$D_2$" 68 of the medium-frequency component 54, are arbitrarily set to 40% and 15% of full scale, respectively. The realistic choice of a relatively small glue-line amplitude 58 will serve to demonstrate how the method of the invention determines the otherwise unknown, and small, glue-line amplitude 58, in the presence of unknown, significantly larger, background signal variations 52, 54.

Figure 4:
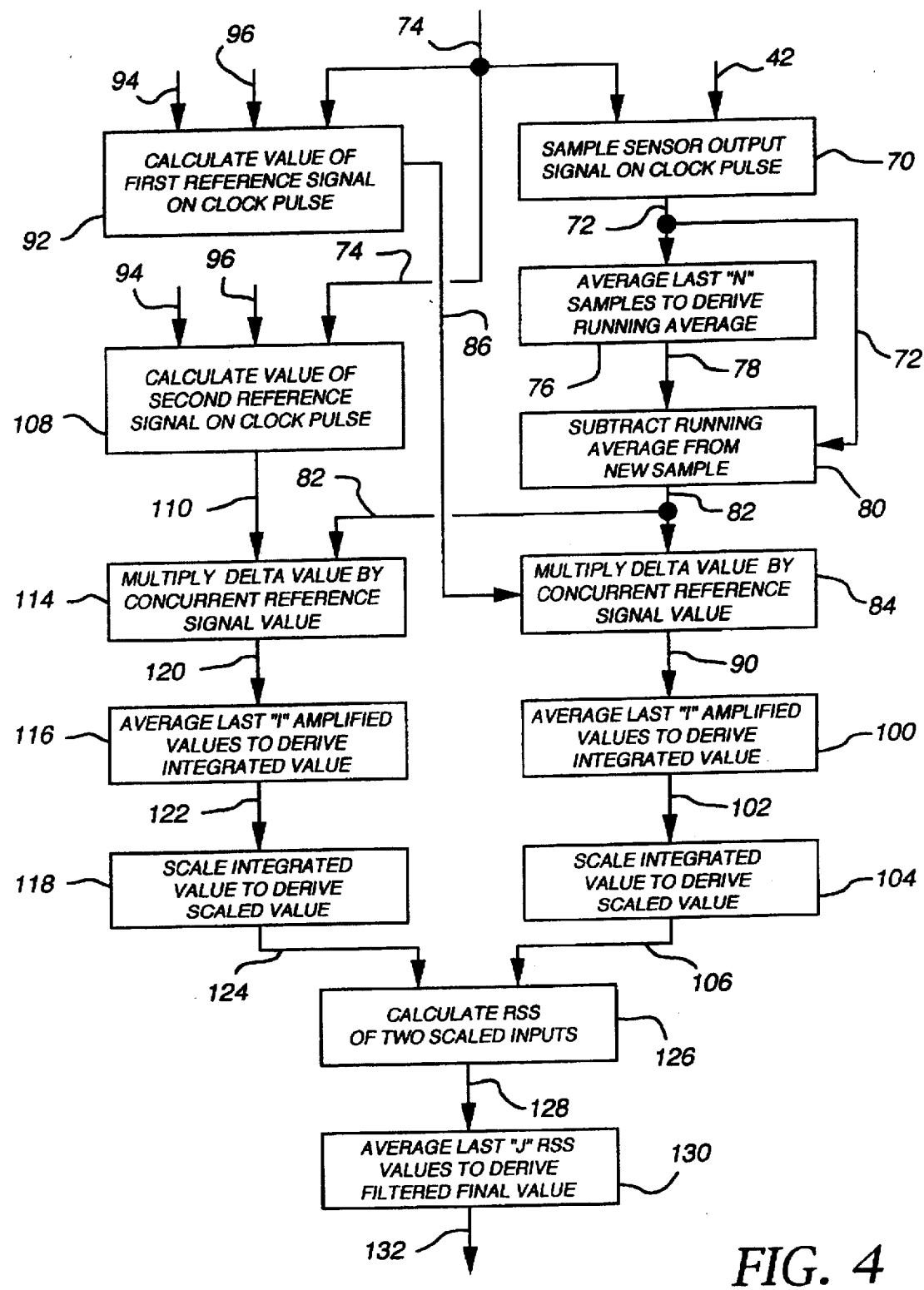
FIG. 4 is a flow chart of the steps performed by the method of the present invention to determine the amplitude (peak-to-valley value) of that component of a sensor output signal that is fluctuating at the fluting frequency.
Figure 5A:
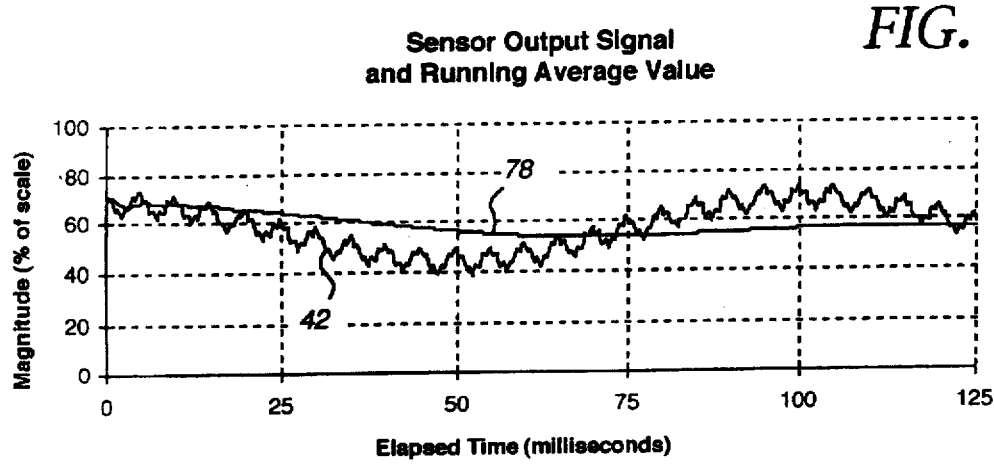
FIGS. 5a to 5k are graphs illustrating the use of phase-locking to determine the amplitude of a signal component of known frequency (i.e. the fluting frequency).
Figure 5B:
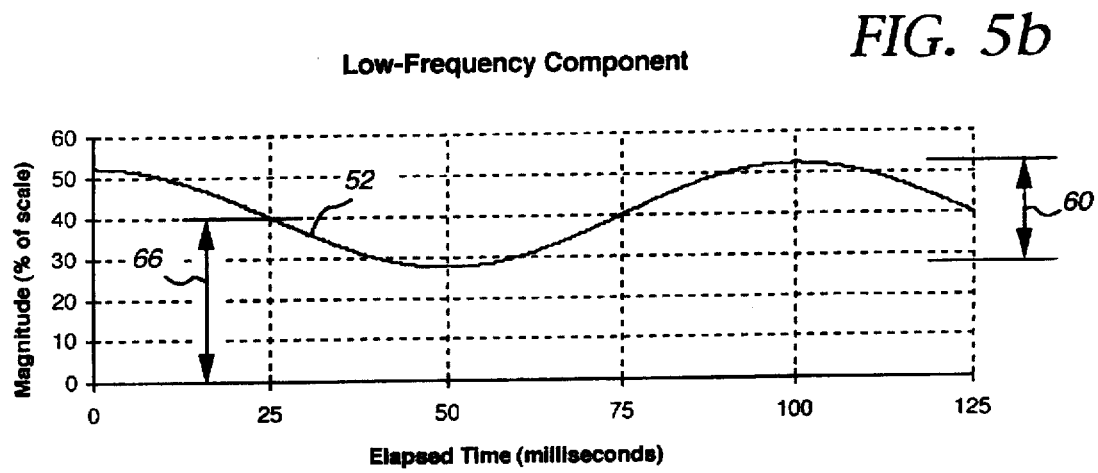
Figure 5C:
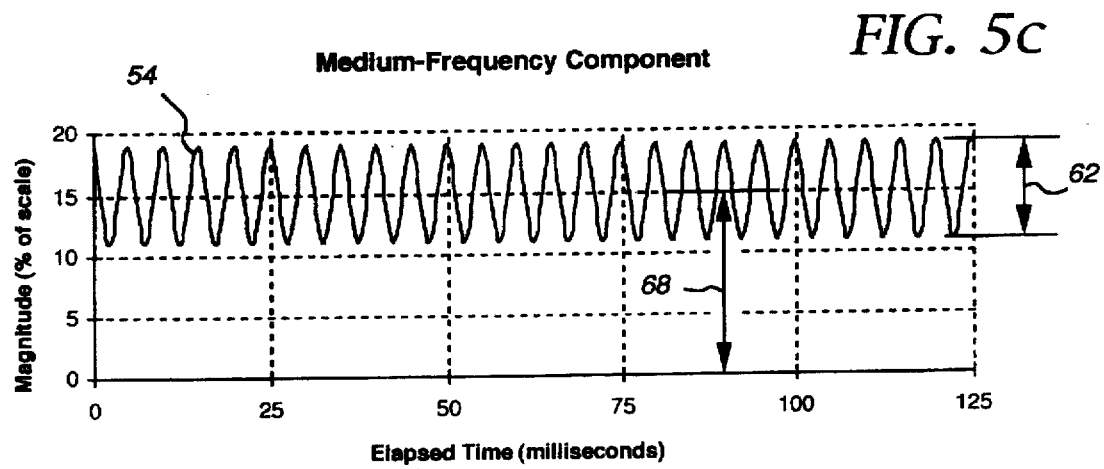
Figure 5D:
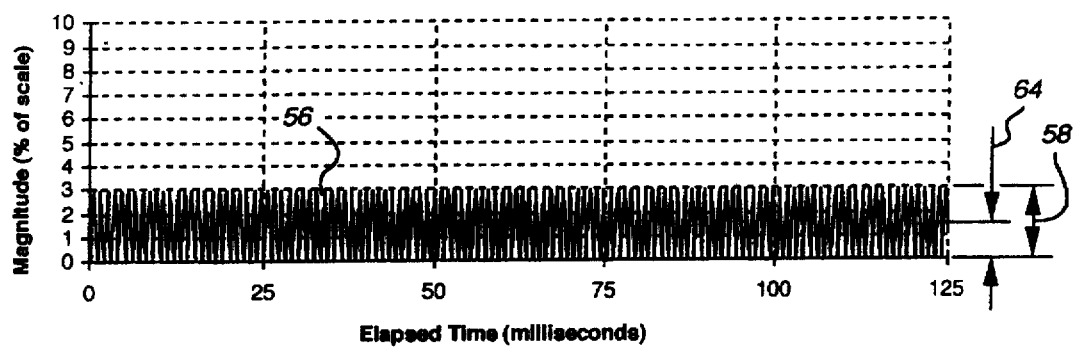

Referring still to FIG. 4 and FIGS. 5a through 5k, the signal processing steps of a suitable implementation of the phase-locking method will now be described. In step 70 the sensor output signal "g(t)" 42 is sampled at a suitably rapid rate (e.g. 10 kHz) to produce digitized signal samples 72. A simple way to control the rate at which the sensor output signal 42 is sampled is to use a clock pulse 74 (that has a configurable pulse period "$\delta t$") to initiate the sampling task with every new clock pulse 74. Then, every time a new sample 72 is generated, step 76 averages the last "N" signal samples 72 to develop am updated, running average value "$<g(t)>_T$" 78 (FIG. 5a). The quantity "N" used in step 76 is a configurable variable, such that the product of "N" and "$\delta t$", being equal to "T", is typically greater than the period of the longest frequency component 52 of the sensor output signal 42. The running average value 78 may therefore be represented by the following mathematical relationship;

$$<g(t)>_T=(1/T)\times\int^T g(t)dt=D_1+D_2+D_3$$

Figure 5E:
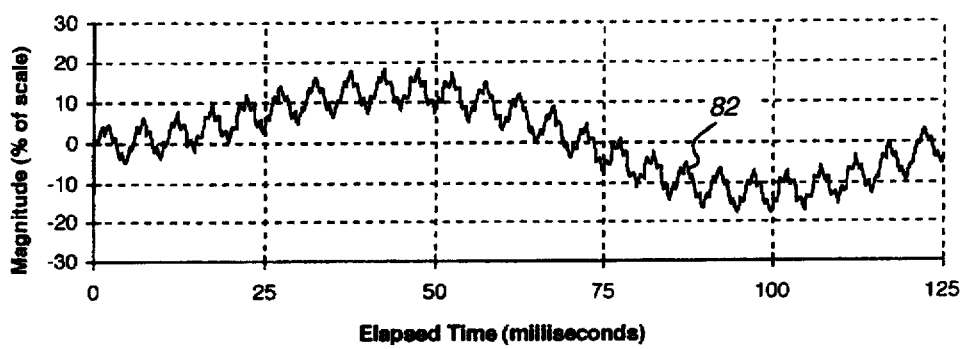
Figure 5F:
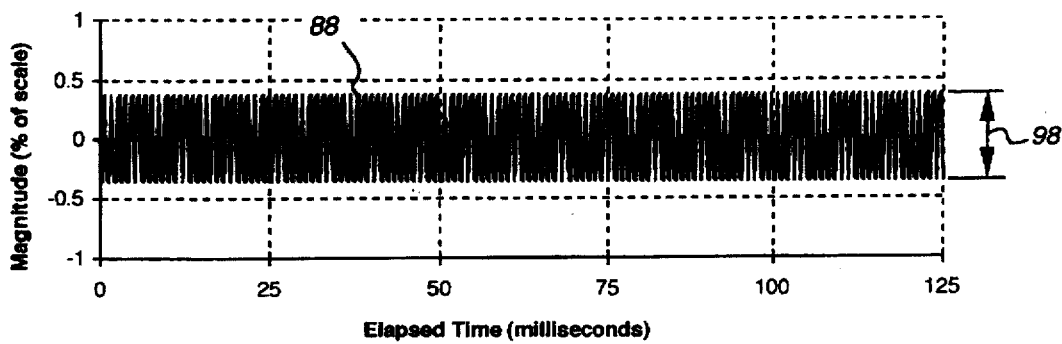

In step 80 each updated running average value 78 is subtracted from each new signal sample 72 to obtain the difference between each new signal sample 72 and the updated running average value 78, with each successive value 82 generated by this step 80 being referred to as a new delta value "g'(t)" 82 (FIG. 5e). The delta value 82 may therefore be represented by the following mathematical relationship:

$$g'(t)=g(t)-<g(t)>_T=\Sigma(A_n/2)\times\cos(\omega_n\times t),$$

for n=1 to N=3 for this example where N=3 for this example

While steps 76 and 80 are not absolutely necessary, they serve to normalize the data by removing the DC offsets 64, 66, 68 of the sensor output signal components 52, 54, 56, which must otherwise be filtered-out by alternate methods later in the processing sequence.

Figure 5G:
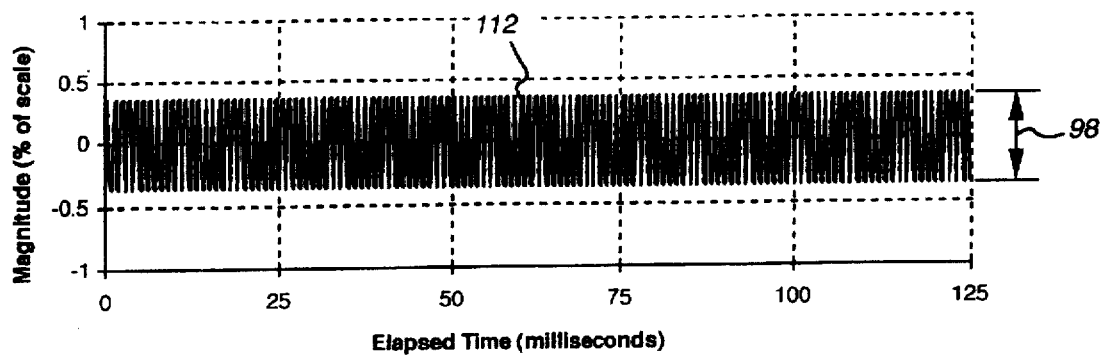
Figure 5H:
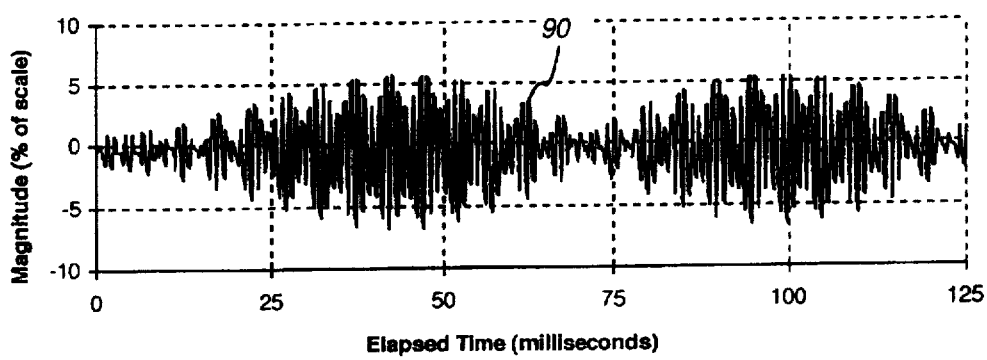
Figure 5I:
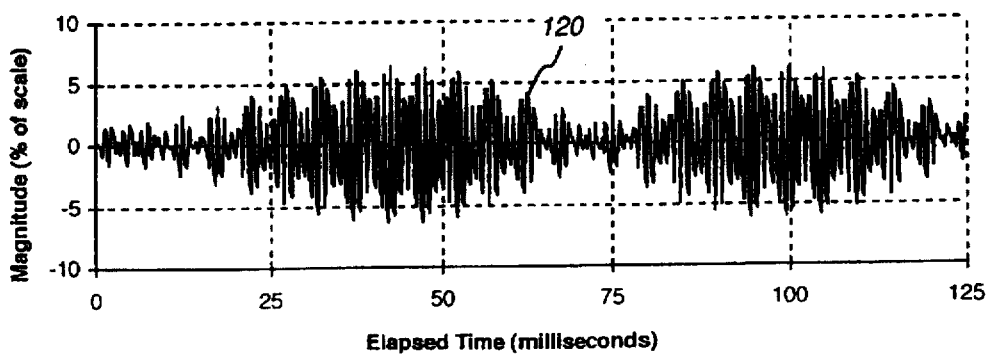

In step 84, each new delta value 82 is then multiplied by the time-dependent, calculated value 86 of a mathematically-defined first reference signal "$r_1(t)$" 88 (FIG. 5f) to generate an amplified value "$h_1(t)$" 90 (FIG. 5h). The time-dependent calculated value 86 is determined in step 92 by means of a suitable trigonometric relationship, whereby "$r_1(t)$" is made to be a function of the elapsed time since the phase-locking procedure was initiated, an input value 94 which is equal to the known fluting roll tooth pitch 50 (as illustrated in FIG. 3a), the monitored machine speed 96, and an arbitrary amplitude "$A_r$" 98. To measure the characteristics of the glue-lines 20 which are used to bond the singleface liner 24 to the medium 12 (as illustrated in FIGS. 1 and 3a), the speed 96 of the singleface liner 24 would be used as the speed input 96. The speed 96 of the singleface liner 24 may be monitored using a shaft encoder or tachometer to measure the rotational speed (i.e. rpm) of an appropriate rotating element of known diameter, such as either of the fluting rolls 14, 16. Similarly, to measure the characteristics of the glue-lines 28 which are used to bond the singleface web 26 to the doubleface liner 32 (as illustrated in FIGS. 1 and 3b), the speed 96 of the doubleface liner 32 would preferably be used as the speed input 96. The speed 96 of the doubleface liner 32 may be monitored using a shaft encoder or tachometer to measure the rotational speed of a contacting rotating element of known diameter. The clock pulse 74 is also used in step 92 to ensure that each new calculated value 86 is synchronized with each new, concurrent sample 72 of the sensor output signal 42. Suitable relationships for deriving the time-dependent calculated value 86 of the mathematically-defined first reference signal 88, and for subsequently deriving the amplified value 90 are therefore:

$r_1(t)=(A_r/2)\times\cos[(\omega_3\times t)+\phi]$, and $h_1(t) = g'(t)\times r_1(t)$ The purpose of step 84 is to amplify that component of the sensor output signal 42 that is synchronized with the first reference signal 88, and to filter-out those components of the sensor output signal 42 that have different frequencies than the first reference signal 88.

Figure 5J:
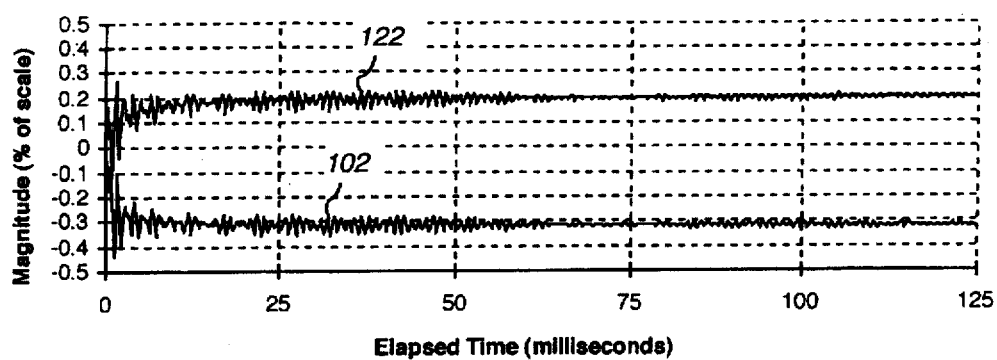
Figure 5K:
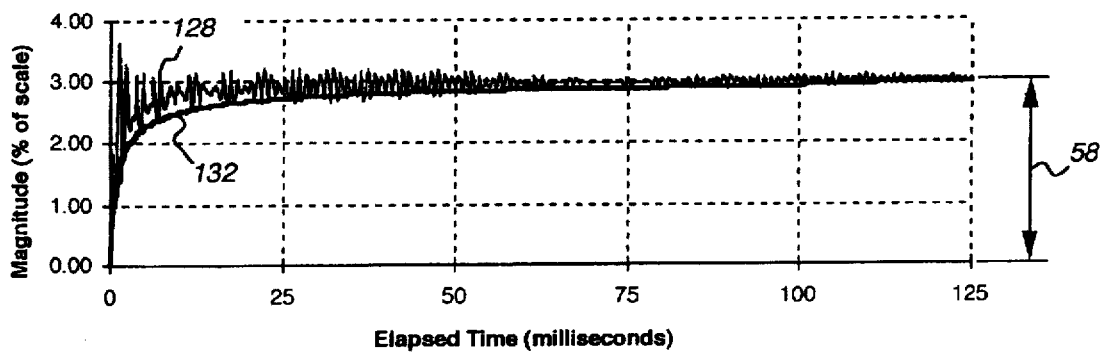

In step 100 the last "T" amplified values are then averaged to develop a running average value 102 which shall be referred to as an integrated value "$<h_1(t)>_T$" 102 (FIG. 5j). The quantity "T" used in step 100 is a configurable variable, such that the product of "T" and "δt", being equal to "T", is typically greater than the period of the longest frequency component 52 of the sensor output signal 42. The integrated value 102 may therefore be represented by the following mathematical relationship:

$$<h(t)>_T = (1/T) \times \int^T h_1(t)dt \approx A_3 \times A_r \times (1/8) \times \cos(\phi)$$

In step 104 each new integrated value 102 is then scaled by dividing it by the amplitude 98 of the first reference signal, and then multiplying the result by eight (8), to produce a scaled value "$h_1'$" 106. The scaled value 106 may therefore be represented by the following mathematical relationship:

$$h_1'=<h_1(t)>_T \times 8/A_r$$

To account for the likely possibility that in a realistic application the first reference signal 88 is somewhat out of phase (i.e. by the amount "$\phi \times 180/\pi$" degrees) with the oscillating glue-line component 56 of the sensor output signal 42, a parallel sequence repeats the functions performed in steps 92, 84, 100, and 104. This parallel sequence begins with step 108, which determines the concurrent, time-dependent, calculated value 110 of a mathematically-defined second reference signal "$r_2(t)$" 112 (FIG. 5g). The second reference signal 112 has the same frequency and amplitude 98 as the first reference signal 88, but is ninety (90) degrees out of phase with the first reference signal 88. A suitable trigonometric relationship for deriving the time-dependent calculated value 110 of the mathematically-defined second reference signal 88 is therefore:

$$r_2(t)=(A_r/2)\times\cos[(\omega_3\times t)+\phi+\pi/2]$$

Steps 114, 116 and 118 perform the same functions as steps 84, 100 and 104, respectively. The intermediate results of this parallel sequence are amplified values "$h_2(t)$" 120 (FIG. 5i) and integrated values "$<h_2(t)>_T$" 122 (FIG. 5j), culminating in the derivation of a second stream of scaled values "$h_2'$" 124. Suitable relationships for deriving the amplified values 120, integrated values 122, and scaled values 124 are therefore:

$$h_2(t) = g'(t) \times r_j(t)$$

$$<h_2(t)>_T = (1/T) \times \int^T h_1(t)dt \approx A_3 \times A_r \times (1/8) \times \sin(\phi)$$

$$h_{2'} = <h_2(t)>_T \times 8/A_r$$

In step 126 the root-sum-square (i.e. the RSS, or square-root of the sum of the squares) of the scaled values 106, 124 is calculated, to produce an RSS value 128 (FIG. 5k) which is a phase-independent measurement of the amplitude 58 of the glue-line component 56. The RSS value 128 may therefore be represented by the following mathematical relationship:

$$h'=[(h_1')^2+(h_2')^2]^{1/2}=A_3\times[\cos^2\phi+\sin^2\phi]^{1/2}=A_3=\text{amplitude of glue-line component}$$

The final, optional step 130 then averages the last "J" RSS values 128 to develop a running average 132 (FIG. 5k) that is the final, filtered value 132, which is approximately equal to the glue-line amplitude 58. The quantity "J" used in step 130 is a configurable variable, such that the product of "J" and "δt", being equal to "T", is typically greater than the period of the longest frequency component 52 of the sensor output signal 42.

It should be noted that some of the filtering steps described above are optional. While steps 100 and 116 are necessary, steps 76, 80 and 130 are not critical. Essentially, the degree of filtering required (such as the number of averaging steps, as well as the number of samples in a running average) depends on the noise level of the original sensor output signal 42, and the desired response time of the measurement (i.e. how fast the measurement processing routine should be able to recognize a meaningful change in the amplitude 58 of the glue-line component 56 of the sensor output signal 42).

Referring again to FIGS. 4 and 5a through 5k, the described phase-locking procedure will produce a value 132 which is approximately equal to the amplitude 58 of the glue-line component 56 of the sensor output signal 42, whether the glue-line component 56 is representative of starch mass or the difference between the glue's temperature and that of the paper behind it. In the case of starch mass, this value 132 is the desired final value, as it represents the starch mass per unit of board surface. However, in the case of temperature measurement, this value 132 represents the differential temperature, not a desired absolute value. Accordingly, one half of the glue-line amplitude 58 (which is equal to the value 132) must be added to, and subtracted from, the sensor output signals running average value 78 to determine the absolute temperatures of the glue and paper substrate, respectively.

Referring again to FIGS. 1, 3a and 3b, the method of the present invention may be used to process the output signal 42, 44 of any suitable sensor 38, 40. In practice, on-line measurement of the machine-direction 10 starch application rate and the cross-machine starch distribution are of primary interest. To measure the amount of applied starch 20, 28 in an on-line environment, a direct or indirect starch mass measurement is required. A preferred way to indirectly measure the starch mass is to measure the amount of infrared radiation that is absorbed at specific wavelengths when the glue-lines 20, 28 are irradiated by infrared light.

Figure 6:
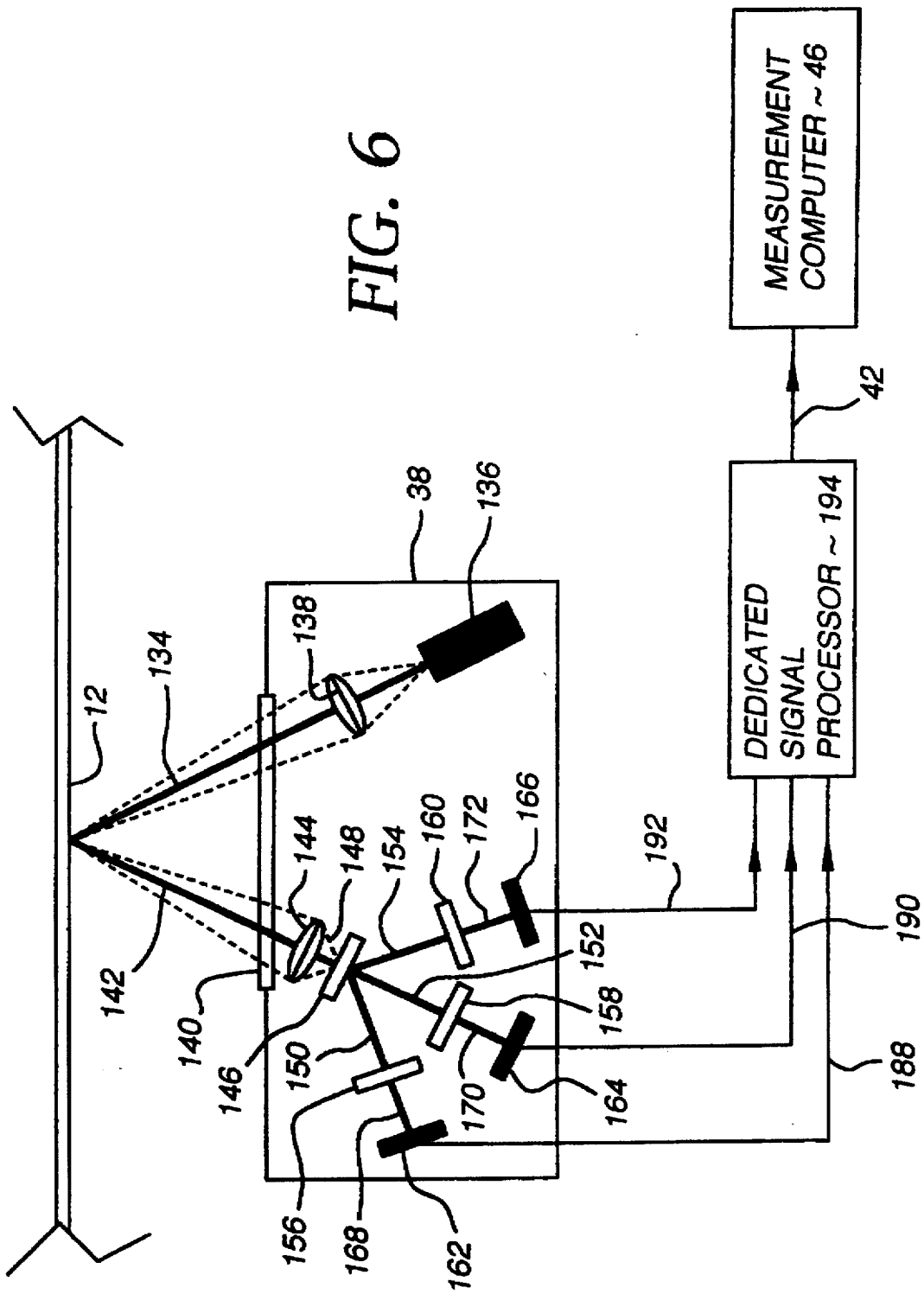
FIG. 6 is a schematic view of an infrared absorption sensor whose output signal is utilized in the system and method of the present invention.

Referring now to FIG. 6, the general operating principles of infrared absorption sensors 38 is well known in the art. A particular implementation suitable for measurement of starch on corrugated board shall now be described. Infrared light 134 is produced by an infrared lamp 136, then passed through a focusing lens 138 and window 140 prior to illuminating the surface of the material 12 being measured. The incident light 134 is then partially absorbed, with the remaining, diffuse infrared light being reflected off material 12. A portion 142 of this diffuse, reflected light then passes through the window 140, a focusing lens 144 and beam-splitter 146, which partitions the focused reflected light 148 into three or more light beams 150, 152, 154. The light beams 150, 152, 154 then pass through accompanying optical band-pass filters 156, 158, 160 onto the active surfaces of accompanying, light-sensitive detectors 162, 164, 166 (i.e. lead-sulfide detectors), which produce electrical output signals 188, 190, 192 whose voltages are proportional to the intensity of the incident light beams 150, 152, 154.

Figure 7:
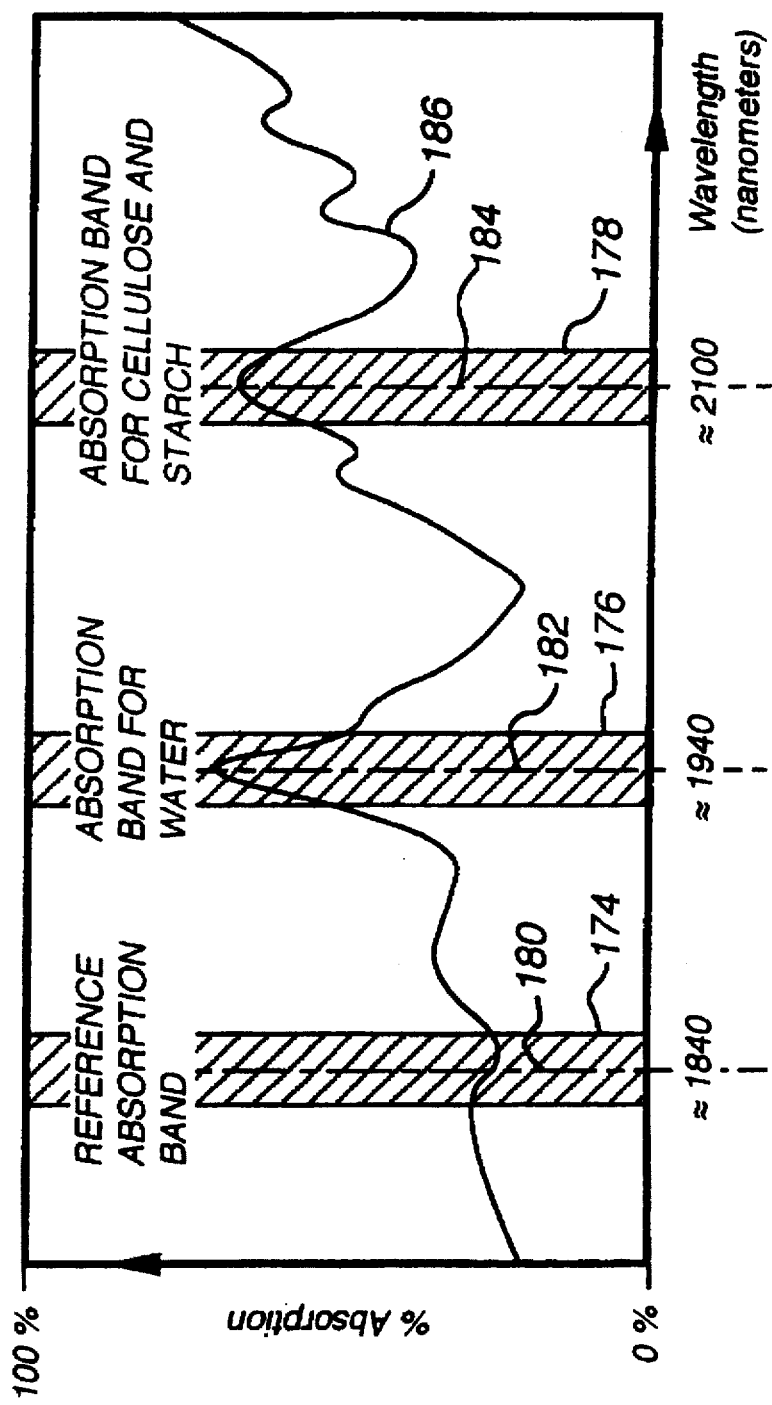
FIG. 7 is a graphical illustration of the infrared absorption spectrum for corrugated board.

Referring now to FIGS. 6 and 7, the optical band-pass filters 156, 158, 160 are designed to limit the light 168, 170, 172 incident upon the detectors 162, 164, 166 to chosen narrow passbands 174, 176, 178 centered about specific wavelengths 180, 182, 184. Suitable band-pass filters 156, 158, 160 have a dielectric coating whose thickness determines the center of the filters passband, and are designed such that the breadth of each filtered light beam's passband 174, 176, 178 is typically limited to about ±20 nanometers, such that the light beams 168, 170, 172 incident upon the detectors 162, 164, 166 are effectively monochromatic. Light beam 150 is filtered by a filter 156 that is chosen to pass light 168 within a reference absorption band 174 centered about wavelength 180 which is approximately 1840 nanometers, at which the percent absorption 186 is relatively insensitive to the amount of cellulose, starch or water that is in or on the measured material 12 (i.e. a 10% change in the mass of cellulose, starch or water produces a less than 1% change in infrared absorption). Light beam 152 is filtered by a filter 158 that is chosen to pass light 170 within a water absorption band 176 centered about wavelength 182 which is approximately 1940 nanometers, at which the percent absorption 186 is very sensitive to the amount of water that is in or on the measured material 12, while being relatively insensitive to the amount of cellulose and/or starch that is in or on the measured material 12 (i.e. a change in water mass produces a ten-fold greater change in infrared absorption than an equal change in starch or cellulose mass). Light beam 154 is filtered by a filter 160 that is chosen to pass light 172 within a cellulose/starch absorption band 178 centered about wavelength 184 which is approximately 2100 nanometers, at which the percent absorption 186 is very sensitive to the amount of cellulose and/or starch that is in or on the measured material 12, while being relatively insensitive to the amount of water that is in or on the measured material 12 (i.e. a change in starch or cellulose mass produces a ten-fold greater change in infrared absorption than an equal change in water mass). As indicated above, the preferred measurement wavelengths 180, 182, 184 are typically 1840, 1940 and 2100 nanometers, respectively, but slight shifts may be required to achieve optimum results.

The electrical output 188, 190, 192 of each detector 162, 164, 166 therefore represents the intensity of the focused reflected light 148 at each chosen wavelength 180, 182, 184. The ratio of one detector output to another is then derived using a computer-based signal processor 194 that is typically dedicated to the task. Dividing one detector output by another produces normalized intermediate results that are representative of percent absorption. This procedure also compensates for fluctuations in the strength of the light-source 136, as well as contamination of common optical components 138, 140, 144, 146.

The starch content of the irradiated surface 12 may then be determined by applying the signal processing steps illustrated in FIG. 4 to a sensor output signal 42 that has been derived from the original detector outputs 188, 190, 192 using an appropriate set of relationships. These relationships combine the outputs of each detector 188, 190, 192 to derive an empirical result which is calibrated to represent the starch content. A suitable set of such relationships is:

$$R_m = (100-Z_r)/(100-Z_m)$$

$$R_c = (100-Z_r)/(100-Z_c)$$

$$W_m = A \times (R_m-1) = A \times (Z_m-Z_r)/(100-Z_m)$$

$$W_{c,s} = B \times (R_c-1) = B \times (Z_c-Z_r)/(100-Z_c)$$

$$W = (C \times W_m) + (D \times W_{c,s}) + E$$

Where;

$D_r$ is the output of the reference detector 162

$D_m$ is the output of the moisture detector 164

$D_c$ is the output of the cellulose/starch detector 166

$W_m$ is the mass of water in the irradiated region of the measured material 12

$W_{c,s}$ is the mass of the cellulose and starch in the irradiated region of the measured material 12

W is the sensor output signal 42, which is subsequently processed by the phase-locking method A, B, C, D and E are empirical constants which are determined by calibration tests that compare known starch mass to the sensor output signal 42. The value of these constants may be optimally determined using common linear regression techniques.

In a conventional application of an infrared absorption sensor to the measurement of corrugated board, paper fiber, bound water, and contaminants such as starch and latex, which are prevalent in papers made from recycled fiber, will absorb infrared radiation at the same wavelengths 182, 184 as the starch-based, aqueous glue. Hence, in a conventional application of infrared absorption technology the above relationships will not produce a sensor output signal "W" 42 that accurately represents the amount of starch on the medium's flute-tips. However, by using a measurement computer 46 to apply the phase-locking method described herein, so as to further process the sensor output signal "W" 42 which is conveyed from the dedicated processor 194 to the measurement computer 46, the oscillating glue-line component 56 of the sensor output signal 42 may be isolated and its calibrated amplitude 58 accurately determined.

A secondary benefit of the signal processing method of the present invention is that the phase-locking procedure eliminates the need to modulate the light source 134 and synchronously demodulate the detector outputs 188, 190, 192 in order to filter-out the effects of power supply noise and fluctuations in ambient infrared radiation, whether the latter originates from the web 12 itself or from surrounding light sources. This benefit derives from the fact that only variations in the focused, reflected infrared light 148 that have a frequency equal to or higher than the fluting frequency, will be recognized by the signal processing method of the present invention.

Figure 8:
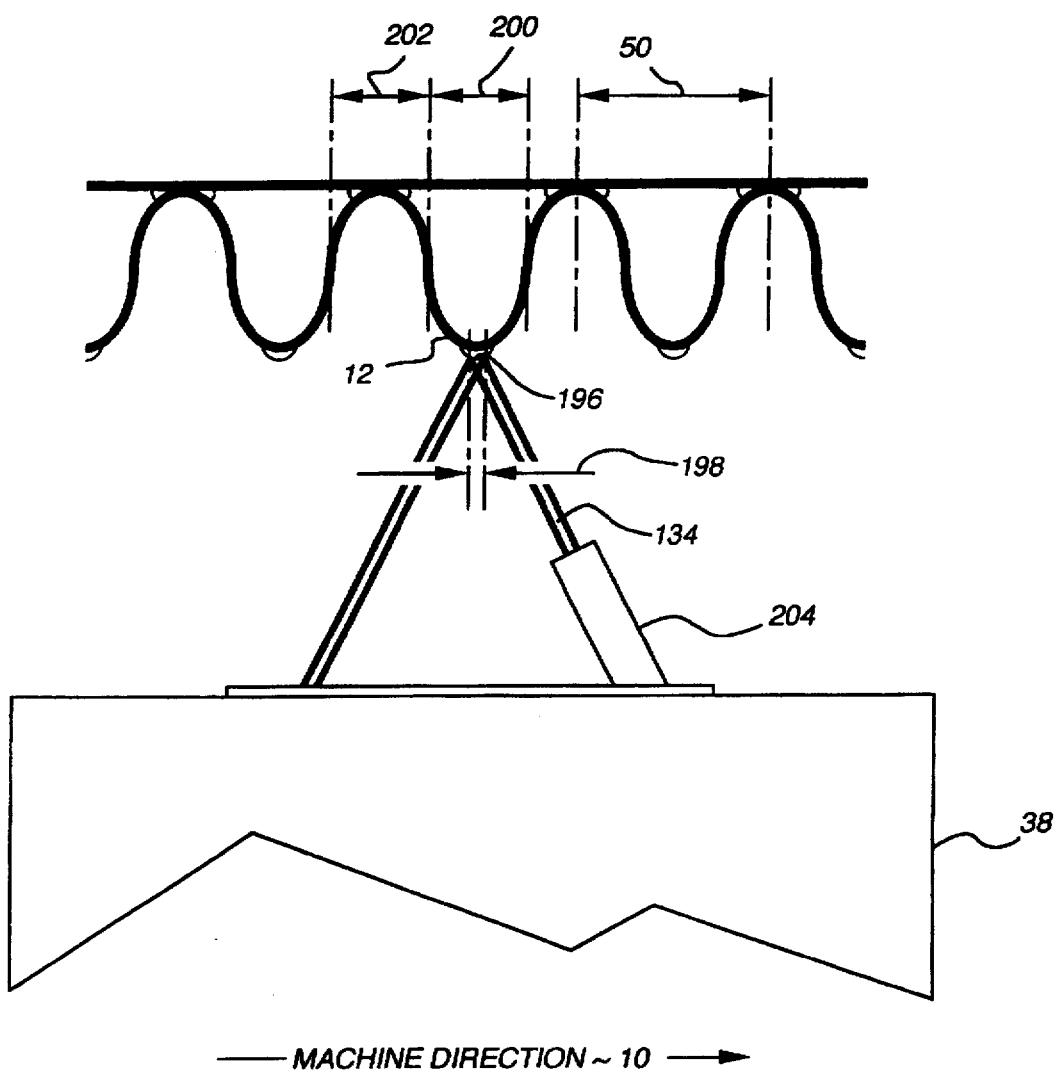
FIG. 8 is a side elevational schematic view of an infrared absorption sensor utilized in the system and method of the present invention, showing key dimensional relationships between the incident infrared light beam and the fluted surface of the measured material.

Referring now to FIG. 8, a suitable sensor 38, whether for the purpose of measuring starch mass or glue temperature, must have a measurement spot 196 with a machine-direction dimension 198 that is smaller than the flute pitch 50. In practice, to differentiate the characteristics of the flute tip region 200 from those of the flute valley region 202, the measurement spot 196 should have a dimension 198 that is less than one third the flute pitch 50. On a typical corrugating line, with a flute pitch of about 0.2 inches, the spot dimension 198 must therefore be less than approximately 0.07 inches. In the case of an infrared absorption sensor, a high intensity infrared light spot 196 with a dimension 198 of this size, or even smaller, may be generated by conveying the focused infrared light 134 to the surface of the measured material 12 through a fiber optic probe 204 whose exit is in close proximity to the measured surface 12 (i.e. within a fraction of an inch).

A suitable sensor 38, regardless of the glue-line characteristic being measured, should also have a response time shorter than about 0.33 milliseconds such that on an application with a fluting frequency of 1,000 Hz or less, the sensor will be able to produce a minimum of three (3) measurements per flute (i.e. 1,000/(3×1,000)=0.33).

Figure 9:
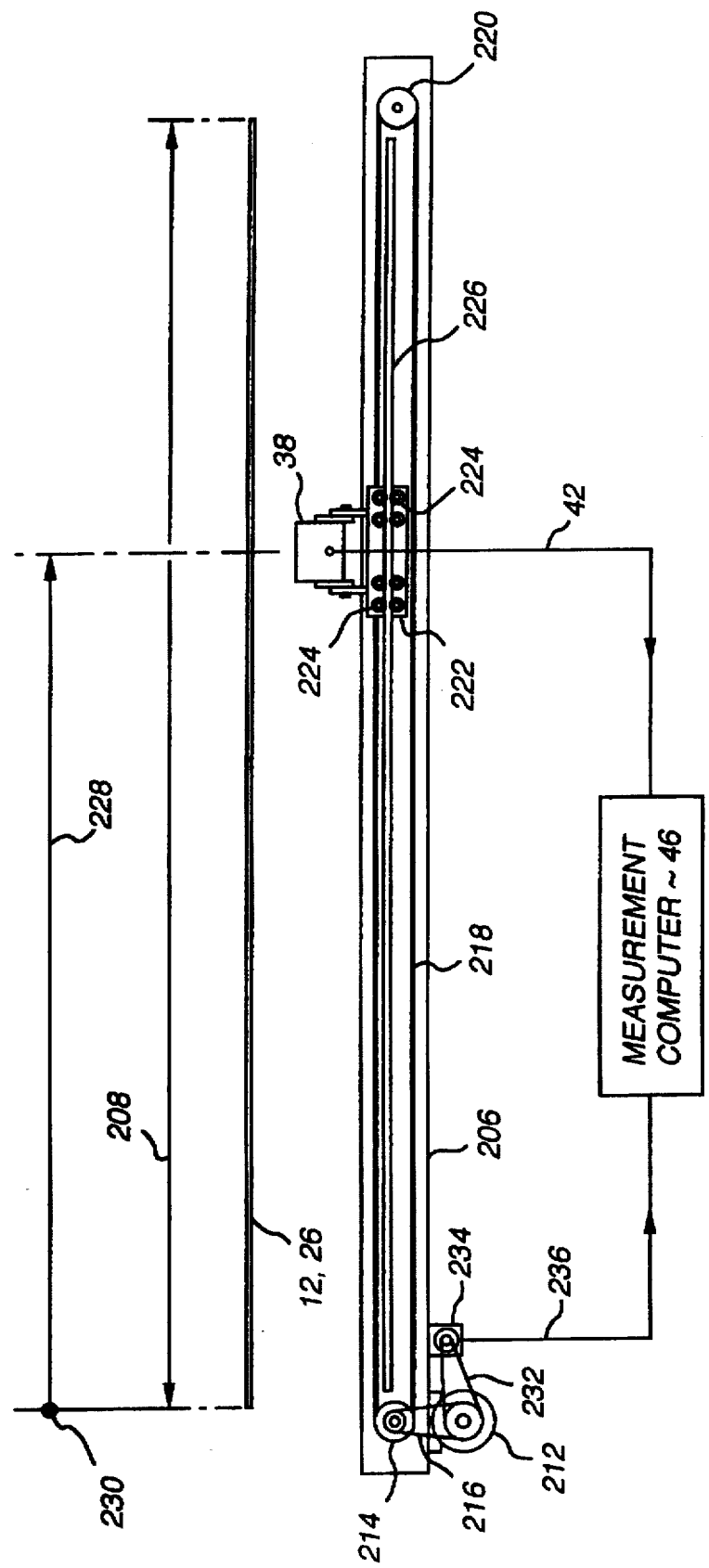
FIG. 9 is an elevational view of a full-width corrugated board, illustrating a traversing mechanism to which is attached a sensor whose output signal is processed using the method of the present invention.

Referring now to FIG. 9, a sensor 38 whose output signal 42 is processed by the method of the present invention is preferably mounted on a traversing mechanism 206, so that it may take measurements at a plurality of sequential points across the cross-direction width 208 of the medium 12 or singleface web 26. A suitable traversing mechanism 206 employs a drive motor 212 which drives a drive pulley 214 by means of an inter-connecting toothed drive belt 216. The drive pulley 214 then drives a full-width belt 218 which runs around an idler pulley 220 that is located at the opposite end of the traversing mechanism 206. The full-width belt 218 is also attached at both ends to a sensor carriage 222. The sensor carriage 222 includes wheels 224 which roll on a full-width track 226, so as to allow the sensor carriage 222 to freely traverse the web 12, 26 along a flat line when it is pulled by the full-width belt 218. To track the cross-machine position 228 of the sensor 38, relative to a suitable datum 230, the traversing mechanism may also include a timing belt 232 which drives a rotary encoder 234. The encoder 234 generates a stream of output pulses 236 at the rate of "x" pulses per inch of sensor travel. The encoder pulses 236 are then fed to the measurement computer 46 which integrates them to compute the cross-machine position 228 of the sensor 38 at fixed time intervals during its progress across the width 208 of the web 12, 26. The computer 46 then pairs each sequential glue-line measurement with a concurrent, computed cross-machine position 228 value, to develop a cross-machine profile of the measured glue-line characteristic.

While the foregoing invention has been described with reference to its preferred embodiments, various alterations and modifications will occur to those skilled in the art. All such alterations and modifications are intended to fall within the scope of the appended claims.

What is claimed is:

1. A system for measuring glue line characteristics of corrugated board, said system comprising:
   means for detecting the intensity of a characteristic of said corrugated board and producing an output signal indicative of said intensity;
   means for isolating glue line components of said output signal from all other components of said output signal, said glue line components representing intensity of said characteristic at a glue line, said isolated output glue line components being components of said output signal that oscillate at a known fluting frequency of said corrugated board.

2. The system for measuring glue line characteristics of corrugated board of claim 1 wherein said means for isolating comprises means for filtering out components of said output signal which are less repetitive and have a lower frequency than said glue line components.

3. The system for measuring glue line characteristics of corrugated board of claim 1 wherein said characteristic is glue temperature, said system further comprising:
   means for measuring the temperature of glue applied to a first layer of said corrugated board which is to be bonded to a second layer of said corrugated board, said means for measuring being located in a corrugated board assembly line at a position where said means for measuring can measure said temperature prior to said first and second layers being bonded together, said means for measuring producing at least one glue temperature output signal.

4. The system for measuring glue line characteristics of corrugated board of claim 1 further comprising means for mounting said means for detecting so that said means for detecting traverses said corrugated board across the width of said corrugated board.

5. A system for measuring glue line characteristics of corrugated board, said system comprising:
   means for producing infrared light and illuminating a surface of said corrugated board with said infrared light;
   means for focusing infrared light reflected off said surface of said corrugated board into a light beam;
   means for splitting said light beam into at least two split light beams;
   means for filtering said split light beams to chosen narrow passbands centered around predetermined wavelengths;
   means for determining the intensity of said split light beams after said light beams have been filtered, said intensity being indicative of the starch content of said corrugated board;
   means for isolating glue line components of said output signal from all other components of said output signal, said glue line components representing intensity of said split light beams at a glue line, said isolated output glue line components being components of said output signal that oscillate at a known fluting frequency of said corrugated board.

6. The system for measuring glue line characteristics of corrugated board of claim 5 wherein said means for isolating comprises means for filtering out components of said output signal which are less repetitive and have a lower frequency than said glue line components.

7. The system for measuring glue line characteristics of corrugated board of claim 5 wherein said means for splitting said reflected infrared light splits said reflected infrared light into at least three beams and wherein said means for filtering filters said one of said at least three beams into a narrow passband centered about a wavelength at which a percent of infrared absorption by a measured material is relatively insensitive to cellulose, starch and water.

8. The system for measuring glue line characteristics of corrugated board of claim 7 wherein said wavelength is 1840, nanometers.

9. The system for measuring glue line characteristics of corrugated board of claim 5 wherein said means for splitting said reflected infrared light splits said reflected infrared light into at least three beams and wherein said means for filtering filters said one of said at least three beams into a narrow passband centered about a wavelength at which a percent of infrared absorption by a measured material is sensitive to a quantity of water on and in said measured material.

10. The system for measuring glue line characteristics of corrugated board of claims 9 wherein said wavelength is 1940 nanometers.

11. The system for measuring glue line characteristics of corrugated board of claim 5 wherein said means for splitting said reflected infrared light splits said reflected infrared light into at least three beams and wherein said means for filtering filters said one of said at least three beams into a narrow passband centered about a wavelength at which a percent of infrared absorption by a measured material is sensitive to a quantity of cellulose and starch on and in said measured material.

12. The system for measuring glue line characteristics of corrugated board of claim 11 wherein said wavelength is 2100 nanometers.

13. The system for measuring glue line characteristics of corrugated board of claim 3 wherein said means for splitting said reflected infrared light splits said reflected infrared light into at least three beams and wherein said means for filtering filters
   a first beam of said at least three beams into a narrow passband centered about a wavelength at which a percent of infrared absorption by a measured material is relatively insensitive to cellulose, starch and water,
   a second beam of said at least three beams into a narrow passband centered about a wavelength at which a percent of infrared absorption by the measured material is sensitive to the amount of water that is in and on the measured material,
   a third beam of said at least three beams into a narrow passband centered about a wavelength at which a percent of infrared absorption by the measured material is sensitive to the amount of cellulose and starch in and on the measured material.

14. A method for measuring glue line characteristics of corrugated board, said method comprising the steps of:
   detecting intensity of a characteristic of said corrugated board and producing an output signal indicative of said intensity;
   isolating glue line components of said output signal from all other components of said output signal, said glue line components representing intensity of said characteristic at a glue line, said isolated output glue line components being components of said output signal that oscillate at a known fluting frequency of said corrugated board.

15. The method for measuring glue line characteristics of corrugated board of claim 14 wherein said means for isolating comprises the step of filtering out components of said output signal which are less repetitive and have a lower frequency than said glue line components.

16. The method for measuring glue line characteristics of corrugated board of claim 14 wherein said characteristic is glue temperature, said method further comprising the step of:
   measuring with temperature sensors the temperature of glue applied to a first layer of said corrugated board which is to be bonded to a second layer of said corrugated board, said temperature sensors being located in a corrugated board assembly line at a position where said temperature sensors can measure said temperature prior to said first and second layers being bonded together, said temperature sensors producing at least one glue temperature output signal.

17. The method for measuring glue line characteristics of corrugated board of claim 14 further comprising the step of mounting at least one sensor for detecting the intensity of said characteristic so that at least one sensor traverses said corrugated board across the width of said corrugated board.

18. A method for measuring glue line characteristics of corrugated board, said method comprising the steps of:
   producing infrared light and illuminating a surface of said corrugated board with said infrared light;
   focusing infrared light reflected off said surface of said corrugated board into a light beam;
   splitting said light beam into at least two split light beams;
   filtering said split light beams to chosen narrow passbands centered around predetermined wavelengths;
   determining the intensity of said split light beams after said light beams have been filtered, said intensity being indicative of the starch content of said corrugated board;
   isolating glue line components of said output signal from all other components of said output signal, said glue line components representing intensity of said split light beams at a glue line, said isolated output glue line components being components of said output signal that oscillate at a known fluting frequency of said corrugated board.

19. The method for measuring glue line characteristics of corrugated board of claim 18 wherein said step of isolating comprises the step of filtering out components of said output signal which are less repetitive and have a lower frequency than said glue line components.

20. The method for measuring glue line characteristics of corrugated board of claim 18 wherein said step of splitting said reflected infrared light comprises splitting said reflected infrared light into at least three beams and wherein said step of filtering comprises filtering said one of said at least three beams into a narrow passband centered about a wavelength at which a percent of infrared absorption by a measured material is relatively insensitive to cellulose, starch and water.

21. The method for measuring glue line characteristics of corrugated board of claim 20 wherein said wavelength is 1840 nanometers.

22. The method for measuring glue line characteristics of corrugated board of claim 18 wherein said step of splitting said reflected infrared comprises splitting said reflected infrared light into at least three beams and wherein said step of filtering comprises filtering said one of said at least three beams into a narrow passband centered about a wavelength at which a percent of infrared absorption by a measured material is sensitive to a quantity of water on and in said measured material.

23. The method for measuring glue line characteristics of corrugated board of claim 22 wherein said wavelength is 1940 nanometers.

24. The method for measuring glue line characteristics of corrugated board of claim 18 wherein said step of splitting said reflected infrared light comprises splitting said reflected infrared light into at least three beams and wherein said step of filtering comprises filtering said one of said at least three beams into a narrow passband centered about a wavelength at which a percent of infrared absorption by a measured material is sensitive to a quantity of cellulose and starch on and in said measured material.

25. The method for measuring glue line characteristics of corrugated board of claim 24 wherein said wavelength is 2100 nanometers.

26. The method for measuring glue line characteristics of corrugated board of claim 16 wherein said step of splitting said reflected infrared light comprises splitting said reflected infrared light into at least three beams and wherein said step of filtering comprises filtering
   a first beam of said at least three beams into a narrow passband centered about a wavelength at which a percent of infrared absorption by a measured material is relatively insensitive to cellulose, starch and water,
   a second beam of said at least three beams into a narrow passband centered about a wavelength at which a percent of infrared absorption by the measured material is sensitive to the amount of water that is in and on the measured material,
   a third beam of said at least three beams into a narrow passband centered about a wavelength at which a percent of infrared absorption by the measured material is sensitive to the amount of cellulose and starch in and on the measured material.

* * * * *